United States Patent [19]

Yueng et al.

[11] Patent Number: 5,006,210

[45] Date of Patent: Apr. 9, 1991

[54] MEANS AND METHOD FOR CAPILLARY ZONE ELECTROPHORESIS WITH LASER-INDUCED INDIRECT FLUORESCENCE DETECTION

[75] Inventors: Edwards Yeung, Ames, Iowa; Werner G. Kuhr, Riverside, Calif.

[73] Assignee: Iowa State University Research Foundation, Inc., Ames, Iowa

[21] Appl. No.: 306,071

[22] Filed: Feb. 6, 1989

[51] Int. Cl.$^5$ .................. G01N 27/26; B01D 57/02
[52] U.S. Cl. ................. 204/180.1; 204/299 R
[58] Field of Search ............. 204/290 R, 183.3, 180.1

[56] References Cited

U.S. PATENT DOCUMENTS 4,675,300 6/1987 Zare et al. .................. 204/180.1 X

OTHER PUBLICATIONS

Jorgenson & Lukacs, "Capillary Zone Electrophoresis" *Science* vol. 222 (Oct. 1983) pp. 266-272.
Roach, Gozel, and Zare "Determinaton of Methotrexate and its Major Metabolite, 7-Hydroxymethotrexate, Using Capillary Zone Electropheresis and Laser-Induced Fluorescence Detection" Journal of Chromatography, 426 (1988) 129-140.
Gozel, Gassmann, and Zare "Electrokinetic Resolution of Amino Acid Enantiomers with Copper(II)-Aspartame Support Electrolyte" Anal. Chem., 1987, 59, 44-49.
Gassmann, Kuo, and Zare, "Electrokinetic Separation of Chiral Compounds" Science (15 Nov. 1985) 813-814.
Burton and Sepaniak "Analysis of $B_6$ Vitamers by Micellar Electrokinetic Capillary Chromatography with Laser-Excited Fluorescence Detection" Journal of Chromatographic Science vol. 24, (Aug. 1986) 347-351.
Pawliszyn, J. "Nanoliter Volume Sequential Differential Concentration Gradient Detector" Anal. Chem. (1988), 60, 2796-2801.
Bornhop and Dovichi "Simultaneous Laser-Based Refractive Index and Absorance Determinations within Micrometer Diameter Capillary Tubes" Anal. Chem (1987), 59, 1632-1636.

*Primary Examiner*—John F. Niebling
*Assistant Examiner*—John S. Starsiak, Jr.
*Attorney, Agent, or Firm*—Zarley, McKee, Thomte, Voorhees & Sease

[57] ABSTRACT

A means and method for capillary zone electrphoresis with laser-induced indirect fluorescence detection. A detector is positioned on the capillary tube of a capillary zone electrophoresis system. The detector includes a laser which generates a laser beam which is imposed upon a small portion of the capillary tube. Fluorescence of the elutant electromigrating through the capillary tube is indirectly detected and recorded.

10 Claims, 1 Drawing Sheet

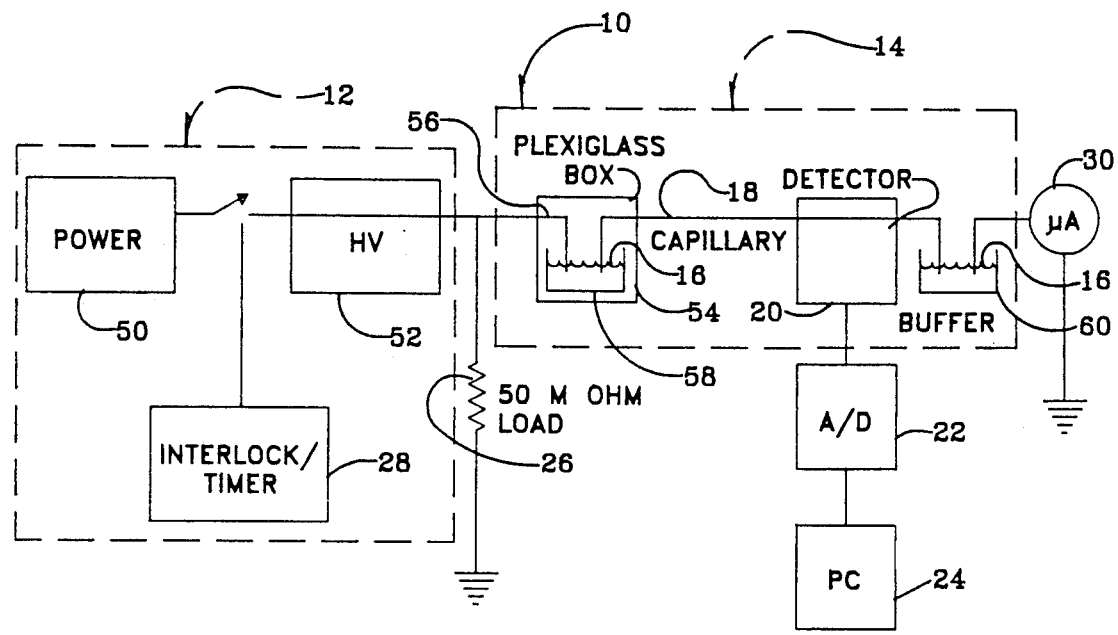
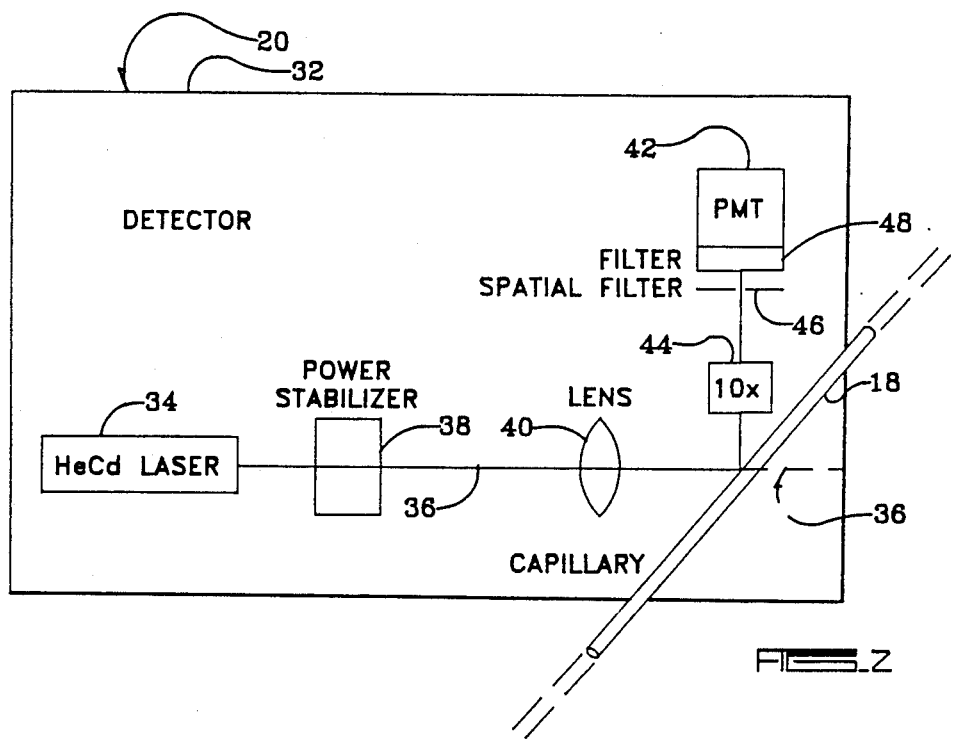

MEANS AND METHOD FOR CAPILLARY ZONE ELECTROPHORESIS WITH LASER-INDUCED INDIRECT FLUORESCENCE DETECTION

GOVERNMENT RIGHTS

This invention was made with government support under contract number W-7405-ENG-82 awarded by the Department of Energy. The Government has certain rights in the invention.

BACKGROUND OF THE INVENTION a. Field of the Invention

The present invention relates to analytical procedures for detection and determination of chemical constituents of substances, and particularly to separation and detection of very low levels of chemical compounds.

b. Problems in the Art

Many analytical procedures exist with respect to attempting to determine the chemical makeup of substances. For example, procedures such as chromotography, electrophoresis, fluorescence detection, and others have been developed for this purpose. Each of those broad categories, in turn, have many different variations.

Each of these methods has its strengths and weaknesses. For example, one type of electrophoresis, namely capillary zone electrophoresis, has very good separation efficiency, for separating out different chemical components, but is limited in its ability to detect what those components are. In many cases, to accurately detect the constituent chemical compounds, additional procedures are required which are very time consuming, and some of which require and result in destruction or alteration of the substance being analyzed.

While many of these analytical methods give what are many times considered acceptable results, these results are many times limited to a selected or narrow group or type of substances. Therefore, problems exist in that there is no adequate universal-type procedure which can separate and detect a wide variety of substances.

Further problems exist with conventional analytical methods with regard to the amount of time required for resolution and derivation of meaningful information, and also with respect to the reliability of the information. Some detection procedures affect the separation process, dilute the sample, or otherwise bring into doubt the reliability of the entire separation and detection process.

Furthermore, with conventional procedures, there are significant problems with respect to getting efficient and accurate information regarding small amounts of materials to be analyzed, or in analyzing materials having small fractional amounts of chemical compounds. This is especially true for materials which have constituent chemical compounds which do not have inherent physical properties such as UV (ultraviolet) or visible absorption, fluorescence, or electrochemical characteristics.

Thus, a primary problem exists for analyzing substances having constituent chemical compounds which are not significantly fluorescing. Such substances are quite abundant in biotechnological and biochemical areas, which are of particular interest.

There is therefore a real need for an improvement in the art with respect to the problems discussed above.

There is a need for an analytical procedure which is more efficient than conventional procedures with regard to time and derivation of results, and which improves the efficiency of separation and detection of chemical constituent compounds. Additionally, there is a need for a procedure that is flexible and applicable to many different types of substances and situations so that it can be used somewhat universally. There is also the need for a procedure which can function efficiently and reliably with regard to small sample amounts or with regard to samples having minute fractional amounts of compounds which are either difficult or impossible to detect by conventional methods.

It is therefore a principal object of the present invention to provide a means and method of capillary zone electrophoresis with laser-induced indirect fluorescence detection which improves over or solves the deficiencies and problems in the art.

A further object of the present invention is to provide a means and method as above described which is reliable and efficient.

A further object of the present invention is to provide a means and method as above described which is fairly universal in its application, yet simple in procedure and in apparatus to accomplish the procedure.

Another object of the present invention is to provide a means and method as above described which is non-destructive, and does not alter the characteristics of the substances being analyzed.

A further object of the present invention is to provide a means and method as above described which saves significant time in deriving results.

Another object of the present invention is to provide a means and method as above described which is operable with respect to very small quantities of sample materials to be analyzed.

Another object of the present invention is to provide a means and method as above described which is reliable with respect to detectibility of minute fractional amounts of chemical compounds.

A further object of the present invention is to provide a means and method as above described which improves and makes more efficient the separation of chemical compounds, the detection of chemical compounds, and the sensitivity to detection of chemical compounds.

A still further object of the present invention is to provide a means and method which is useful for a variety of analytical situations and substances.

Another object of the present invention is to provide a means and method as above described which is useful for non-fluorescing substances.

Another object of the present invention is to provide a means and method as above described which is safe and economical.

These and other objects, features, and advantages of the present invention will become more apparent with reference to the accompanying specification and claims.

SUMMARY OF THE INVENTION

The present invention presents a combination of capillary zone electrophoresis with laser induced indirect fluorescence detection to provide an improvement in the art with regard to separation and detection of chemical components of analyzed substances. An open capillary zone electrophoresis system includes a detector which operates to indirectly measure changes in fluorescence induced by the laser. An output from the detector means can be communicated to a data processing device or a recording means to make a record of such detection correlated to time, and to derive meaningful results.

The invention represents a universal, simple, and efficient analytical procedure, which improves upon the amount of time needed, the separation efficiency, and the detection sensitivity, presenting a reliable and economical analytical tool.

The invention includes various features and options which enhance its results and make it particularly advantageous for reliably deriving information from very small amounts of sample material, and for detecting very small fractional amounts of chemical compounds. Its high sensitivity and universality make it also particularly useful with regard to biochemically important molecules.

BRIEF DESCRIPTION OF THE DRAWINGS

FIG. 1 is a diagrammatic view of an analytical system according to the system.

FIG. 2 is a diagrammatic view of the detector of FIG. 1.

DETAILED DESCRIPTION OF THE PREFERRED EMBODIMENT

The present invention has been described generally above. To assist in an understanding of the invention, a preferred embodiment of the invention will now be described in detail. Reference should be taken to the drawings, namely FIGS. 1 and 2. Reference numerals will be used to designate various components and features in the drawings. Like reference numbers will be used for like parts in each of the Figures.

With particular reference to FIG. 1, a diagrammatic view of preferred embodiment 10 of the invention is shown. A capillary zone electrophoresis system consisting of a power section 12, and a capillary section 14, such as is well known in the art, is utilized. For specifics regarding the components and operation of capillary zone electrophoresis systems, reference is given to Jorgenson and Lukacs, "Capillary Zone Electrophoresis" Science Vol. 222, pgs. 266-272, which is hereby incorporated by reference.

Power section 12 selectively introduces high voltage electricity through capillary section 14. A buffer solution 16 is put in fluid communication with capillary tube 18. A sample or specimen material to be analyzed is injected into one of the open ends of capillary tube 18. Upon application of the high voltage, the sample separates by migrating through the capillary tube 18 according to the reaction of different constituent compounds to the electric field. In other words, ionic components of the specimen or sample migrate through the capillary tube 18 at different speeds based upon their particular electrical characteristics.

Thus, the capillary zone electrophoresis system presents an efficient way of separating constituent chemical compounds of the sample.

A detector 20 is added to the capillary zone electrophoresis system according to the invention. Detector 20 utilizes indirect fluorescence detection principles to derive information and detect the constituent chemical compounds separated by the electrophoresis system as they pass by detector 20. Indirect fluorescent detection is known within the art and one type of this sort of analytical procedure is explained in Mho and Yeung, "Detection Method for Ion Chromatography Based on Double-Beam Laser-Excited Indirect Fluorometry", Analytical Chemistry, 1985, 57, 2253-2256, which is incorporated by reference herein.

It is to be understood that to allow the indirect fluorescence detection part of the invention to operate, a fluorescent ion or fluorophore is added to the buffer solution to become the principal component of the electrophoretic buffer. Thus, when the ionic components of the sample enter detector 20, laser-induced fluorescence results in either displacement or ion-pairing of the ionic analyte with the fluorophore. This produces a signal, from which can be derived the analytical results.

In FIG. 1, it can be seen that an analog signal from detector 20 can be communicated to an analog-to-digital (A/D) converter 22, which interfaces with a computer 24. Thus, the signals can be recorded, analyzed, and manipulated to derive information about the separated and detected constituent chemical components of the sample. It is to be understood, that alternatively, detector 20 could be directly connected to an analog chart recorder as an alternative method of recording the analytical procedure.

It is also to be understood that in FIG. 1, a large resistive load 26 is connected to the electrical line between power section 12 and capillary section 14, and is directed to ground. The preferred embodiment resistive load 26 comprises a 50 megohm (M Ohm), 100 watt resistor array to provide a current shunt to ground by serving as parallel resistance to capillary section 14.

Additionally, an interlock timer component 28 is utilized with power section 12 to protect personnel from the high voltage when utilizing the system, and to coordinate timed injection of the sample and the electrophoresis procedure.

Finally, an ammeter 30 measures current continuously between what will be referred to as the cathode end of capillary section 14 and ground.

FIG. 2 specifically and diagrammatically depicts the structure of detector 20. Capillary tube 18 passes through enclosure 32 of detector 20. A laser 34 producing a laser beam 36 positioned to direct laser beam 36 to capillary tube 18 at a specific location. Laser beam 36 is first passed through power stabilizer 38 and then into focusing lens 40, allowing laser beam 36 to be precisely and narrowly focused in on a small location on capillary tube 18. The angle between the laser and the capillary tube is at Brewster's angle.

Laser beam 36 would then pass through capillary tube 18 but would induce fluorescence changes in the elute which is passing by in capillary tube 18. These fluorescence changes are detected and monitored by PMT detecter 42 which is a photo-multiplier tube such as is known in the art. As shown in FIG. 2, PMT 42 is positioned at an angle from the reflectance of laser beam 36 from capillary tube 18. The fluorescence is imaged onto PMT 42 by a ten power (10x) microscope objective 44. Stray light is minimized by utilizing a spatial filter 46 in front of PMT 42. Finally, an interference filter 48 is positioned directly in front of PMT 42 to isolate certain fluorescence, as desired.

Thus, it can be seen that PMT 42 can be directly connected to A/D converter 22 and computer 24 as shown in FIG. 1 to record detection readings of the fluorescence as a function of time.

In the preferred embodiment shown in FIGS. 1 and 2, the preferred components are as follows:

Power section 12 is comprised of power source 50 which can be conventional residential alternating current (102-130 VAC). High voltage power supply 52 is a 50 kilovolt (kV) Spellman model UHR 50PN150.

The interlock timer component 28 is circuitry which, as is known in the art, automatically disconnects high voltage power source 52 if plexiglass box 54, containing the anodic, high voltage end 56 from high voltage power source 52 is handled. This serves as a safety feature for those using the system. Interlock timer component 28 also contains an electronic timer which is used to control the time of sample injection when samples are introduced by electromigration of the sample solution into capillary tube 18.

Capillary tube 18 in the preferred embodiment is an untreated or silyated 100 centimeter (cm) fused silica capillary. It can be either 50 micrometers inside diameter (i.d.), available from SGE; or 15 micrometers i.d., 150 micrometers outside diameter (o.d.), available from Polymicro Technologies, Phoenix, Ariz. One end of capillary tube 18 is immersed in buffer solution 16 in container 58 within plexiglass box 54. This serves as the "anode" end of capillary tube 18. The other end of capillary tube 18 is immersed into buffer solution 16 in container 60, comprising the "cathode" end of capillary tube 18.

Laser 34 comprises an HeCd (Helium Cadmium) laser of 325 nanometer (nm) wavelength at 8 milliwatts (mW), available from Liconix under product model number 4240. Power stabilizer 38 stabilizes laser beam 36 to within 0.05% by utilizing laser power stabilizer model LS100, available from Cambridge Research and Instrumentation, Cambridge, Massachusetts. The stabilized laser beam at 5 mW is focused onto a small spot on capillary tube 18 (in the preferred embodiment a 15 micrometer spot) with a 1 centimeter (cm) quartz lens 40 available from Melles Griot. In the preferred embodiment utilizing capillary tube 18 with 15 micrometer i.d., and cleared of any polyamide coating, final detection volume is approximately 3 picoliters (pL).

It is to be understood that capillary tube 18 is positioned at Brewster's angle with respect to laser beam 36 at a position near the cathodic end of capillary tube 18 (in the preferred embodiment 10 centimeters from the cathodic end).

The ten power microscope objective 44 and spatial filter 46 are available from commercial vendors, and are well known within the art. PMT 42 is available from Hamamatsu under product designation R928. Interference filter 48 in the preferred embodiment is at 405.1 nm, such as is commercially available as is known in the art, or can be a broad band glass filter available from Corning under product number 2-69, Corning, N.Y.

In the preferred embodiment A/D converter is a five hertz (Hz) converter available from Data Translation under model DT 2827, and computer 24 is an IBM PC/AT.

Appropriate software, such as is well within the skill of those skilled in the art, is utilized with computer 24.

It can therefore be seen that the present invention is operable to be used as a reliable, efficient, and non-complex method of obtaining high sensitivity and efficiency in the detection of chemical components of substances. It does so nondestructively, without the requirement of derivatization, by the indirect fluorescence detection.

The invention is universal in the sense that it is useful for many different types of substances, including non-fluorescing compounds and very small molecular compounds. It is fast in its resolution, and taking only a few minutes for the complete process. It can be used on samples of less than one picomole, and for sample volumes less than two nanoliters (nL). Its detection limit is around fifty attomoles (amol). For non-fluorescing samples, the system can "visualize" the chemical makeup by utilizing the fluorescing species in the eluent.

Application of the invention is particularly useful as to biotechnical and biochemical substances. Examples are nucleic acids and amino acids in DNA sequencing or protein sequencing. Such things as peptides, nucleotides, fatty acids, sugars, and glycolytic intermediates can be detected in their native states, which is generally difficult if not impossible with conventional methods. The procedure of the invention is thus useful in the genetics field, studying metabolism, and even having direct analysis of cells in vivo in clinical applications. Viruses and bacteria can be studied as well as other difficult to detect and analyze substances. The invention is even applicable to studying the chemical composition of single cells, which could have tremendous effect on such things as studying mutagens in cell cultures. The applications and potential advantages are virtually innumerable.

It is believed to be further helpful to describe operation of the invention with regard to the preferred embodiment depicted in FIGS. 1 and 2. Certain enhancements and features will be pointed out. The buffer solution 16 is prepared by choosing a fluorescing anion as part of the buffer solution 16. Containers 58 and 60 are then filled with buffer solution 16. A sample is then dissolved into buffer solution 16 in container 58 and the system is ready to begin.

It is to be understood that to increase the efficiency of the system, prior to use, it is preferred that certain standards are maintained and procedures followed. All chemicals used should be reagent grade unless otherwise noted. All water used should be deionized, such as that available from Millipore, Bedford, Mass.

Pre-preparation of capillary tube 18 consists of silating with trimethoxychlorosilane (alternatively referred to as TCMS, available from Aldrich). This is accomplished by aspirating a 20% solution of TCMS in methylene chloride through capillary tube or column 18. The solvent is evaporated, tube 18 ends are sealed, and tube 18 is then heated at 340-350° C. for one to two hours. Tube 18 is then washed successively with methanol, distilled water, and buffer solution 16 prior to use.

The purpose of silating capillary tube 18 is to minimize interactions between the ions in any injected sample on the surface of capillary tube 18, and thus reduce electroosmotic flow. This in turn plays a significant part in reducing background noise in the indirect fluorescing signal. Both peak-broadening and long-term drift of the separation process are significantly reduced by the deactivation of the capillary tube 18's surface. This in turn allows the use of more dilute buffer solutions (for example, 50 micromoles of salicylate) and provides a much more stable background fluorescence.

The sample is introduced to capillary tube 18 by electromigration from the container 58. This can be accomplished by presenting electrical power through the system for a regulated time period. Resistive load 26 is advantageous in assuring standardization of injections using the electromigration procedure. The amount of sample introduced by this method is dependent on the rate at which capillary tube 18 is charged and discharged. The rise time to maximum voltage is determined by the time constant of high voltage power supply 52. The discharge rate on the other hand is determined by the resistance of load 26. It is to be understood that when only column or tube 18 is present, the fall time is determined by the time constant of the discharge across tube 18, which varies with tube dimensions and buffer concentration. When the resistance of load 26 is much lower than that of tube 18, the discharge rate will be dominated by the time constant determined by load 26. Therefore, use of load 26 will produce shorter, more uniform injections.

By interlocking the power supply to plexiglass box 54, which isolates the anodic high voltage end 56 of the power supply, safety for the operator is obtained. In other words, any handling of container 58, capillary tube 18 (at least at its anodic high voltage end 56), will disable electrical power to plexiglass box 54.

Once a sample is injected into tube 18, detector 20 is powered, and A/D converter 22 and 24 are made ready. Another feature to enhance the reliability and efficiency of the system is to stabilize the output power of laser 34. This stabilization is accomplished by feedback control from power stabilizer 38 which determines the stability of background fluorescence, which in turn are dependent on the stability of the light source and the intensity of fluorescence. Although power stabilizer 38 does reduce laser power significantly using short focal-length focusing lens 40, it is possible to focus to a spot less than 15 micrometers in diameter on tube 18.

Stabilization of laser 34 increases the dynamic reserve by over $10^3$. Because this allows reliable detection of very small detection volumes in tube 18, this results in very high mass sensitivity for detector 20.

Concurrently, improved dynamic reserve also gives significant improvement in separation efficiency. The increase in dynamic reserve allows use of more dilute samples, decreasing sample loading, since the major ionic component in the electrophoretic buffer solution 16 must be the floraphore used to provide the signal.

The system is then operated and fluorescence is collected perpendicular to the plane containing laser beam 36. In one preferred embodiment and method of operation described here, salicylate fluorescence is isolated by interference filter 48 at 405.1 nm. As a sample electromigrates down tube 18, this fluorescence is monitored. Until the sample reaches detector 20, a constant background signal is detected. When the sample reaches detector 20, the interaction with the fluorophor will result in either displacement (for ions of like charge) or ion-pairing (for oppositely charged ions) with the fluorophor. The signal produced is thus independent of the spectral properties of the analyte molecule and combines the innate sensitivity of the fluorescence technique with a much broader spectrum of analysis.

Either a chart recorder or computer 24 monitors the signal and makes a record of it for derivation of ultimate results. It is to be understood that computer 24 can also be programmed to perform digital data operations according to desire.

The included preferred embodiment is given by way of example only, and not by way of limitation to the invention, which is solely described by the claims herein. Variations obvious to one skilled in the art will be included within the invention defined by the claims. It can therefore be seen the invention achieves at least all of its stated objectives.

What is claimed is:

1. A means for capillary zone electrophoresis with laser-induced indirect fluorescence detection comprising:
   a capillary zone electrophoresis system including a capillary tube means having an anode and a cathode end, power means for imposing an electrical field upon the capillary tube means, specimen means for supplying specimen to the capillary tube means, buffer means for supplying buffer to the capillary tube means;
   an indirect fluorescence detection system including a laser means for directing a laser beam upon a selected portion of the capillary tube means, a detector means for detecting fluorescence indirectly from the selected portion of the capillary tube means, the buffer containing as a principal component a fluorescing portion which fluoresces upon imposition of the laser beam and which allows indirect fluorescence detection by causing one of the set of displacement and ion-pairing of the sample and the electrophoresis portion of the buffer without labeling the sample with an electrophoretic portion, the detector measuring a signal independent of the spectral properties of the sample but related to fluorescing changes caused by the displacement or ion-pairing which indirectly allows sensitive detection of constituent components of the specimen during the electrophoresis process; and
   an interlock and timing means associated with the power means for controlling the periods of time the electrical field is created.

2. The means of claim 22 wherein the interlock and timing means includes safety means for disconnecting electrical power from the system.

3. A means for capillary zone electrophoresis with laser-induced indirect fluorescence detection comprising:
   a capillary zone electrophoresis system including a capillary tube means having an anode and a cathode end, power means for imposing an electrical field upon the capillary tube means, specimen means for supplying specimen to the capillary tube means, buffer means for supplying buffer to the capillary tube means;
   an indirect fluorescence detection system including a laser means for directing a laser beam upon a selected portion of the capillary tube means, a detector means for detecting fluorescence indirectly from the selected portion of the capillary tube means, the buffer containing as a principal component a fluorescing portion which fluoresces upon imposition of the laser beam and which allows indirect fluorescence detection by causing one of the set of displacement and ion-pairing of the sample and the electrophoresis portion of the buffer without labeling the sample with an electrophoretic portion, the detector measuring a signal independent of the spectral properties of the sample but related to fluorescing changes caused by the displacement or ion-pairing which indirectly allows sensitive detection of constituent components of the specimen during the electrophoresis process; and a shunting resistor means electrically connected between the power means and the anode end of a capillary tube means.

4. A means for capillary zone electrophoresis with laser induced indirect fluorescence detection comprising:
  a capillary zone electrophoresis system including a capillary tube means having an anode and a cathode end, power means for imposing an electrical field upon the capillary tube means, specimen means for supplying specimen to the capillary tube means, buffer means for supplying buffer to the capillary tube means;
  an indirect fluorescence detection system including a laser means for directing a laser beam upon a selected portion of the capillary tube means, a detector means for detecting fluorescence indirectly from the selected portion of the capillary tube means, the buffer containing as a principal component a fluorescing portion which fluoresces upon imposition of the laser beam and which allows indirect fluorescence detection by causing one of the set of displacement and ion-pairing of the sample and the electrophoresis portion of the buffer without labeling the sample with an electrophoretic portion, the detector measuring a signal independent of the spectral properties of the sample but related to fluorescing changes caused by the displacement or ion-pairing which indirectly allows sensitive detection of constituent components of the specimen during the electrophoresis process; and a power stabilizing means positioned between the laser means and the capillary tube means for stabilizing the laser beam.

5. A means for capillary zone electrophoresis with laser induced indirect fluorescence detection comprising:
  a capillary zone electrophoresis system including a capillary tube means having an anode and a cathode end, power means for imposing an electrical field upon the capillary tube means, specimen means for supplying specimen to the capillary tube means, buffer means for supplying buffer to the capillary tube means;
  an indirect fluorescence detection system including a laser means for directing a laser beam upon a selected portion of the capillary tube means, a detector means for detecting fluorescence indirectly from the selected portion of the capillary tube means, the buffer containing as a principal component a fluorescing portion which fluoresces upon imposition of the laser beam and which allows indirect fluorescence detection by causing one of the set of displacement and ion-pairing of the sample and the electrophoresis portion of the buffer without labeling the sample with an electrophoretic portion, the detector measuring a signal independent of the spectral properties of the sample but related to fluorescing changes caused by the displacement or ion-pairing which indirectly allows sensitive detection of constituent components of the specimen during the electrophoresis process; and an imaging means between the capillary tube means and the detector means for collecting an imaging fluorescence upon the detector means emanating from capillary tube means where the laser means has been directed.

6. A means for capillary zone electrophoresis with laser induced indirect fluorescence detection comprising:
  a capillary zone electrophoresis system including a capillary tube means having an anode and a cathode end, power means for imposing an electrical field upon the capillary tube means, specimen means for supplying specimen to the capillary tube means, buffer means for supplying buffer to the capillary tube means;
  an indirect fluorescence detection system including a laser means for directing a laser beam upon a selected portion of the capillary tube means, a detector means for detecting fluorescence indirectly from the selected portion of the capillary tube means, the buffer containing as a principal component a fluorescing portion which fluoresces upon imposition of the laser beam and which allows indirect fluorescence detection by causing one of the set of displacement and ion-pairing of the sample and the electrophoresis portion of the buffer without labeling the sample with an electrophoretic portion, the detector measuring a signal independent of the spectral properties of the sample but related to fluorescing changes caused by the displacement or ion-pairing which directly allows sensitive detection of constituent components of the specimen during the electrophoresis process; and a filtering means in position between the capillary tube means and the detector means, the filtering means including a spatial filter.

7. A means for capillary zone electrophoresis with laser induced indirect fluorescence detection comprising:
  a capillary zone electrophoresis system including a capillary tube means having an anode and a cathode end, power means for imposing an electrical field upon the capillary tube means, specimen means for supplying specimen to the capillary tube means, buffer means for supplying buffer to the capillary tube means;
  an indirect fluorescence detection system including a laser means for directing a laser beam upon a selected portion of the capillary tube means, a detector means for detecting fluorescence indirectly from the selected portion of the capillary tube means, the buffer containing as a principal component a fluorescing portion which fluoresces upon imposition of the laser beam and which allows indirect fluorescence detection by causing one of the set of displacement and ion-pairing of the sample and the electrophoresis portion of the buffer without labeling the sample with an electrophoretic portion, the detector measuring a signal independent of the spectral properties of the sample but related to fluorescing changes caused by the displacement or ion-pairing which indirectly allows sensitive detection of constituent components of the specimen during the electrophoresis process; and
  a filtering means in position between the capillary tube means and the detector means, the filtering means including an interference filter for selecting desired fluorescence wavelengths to be passed to the detector means.

8. A method of improving the sensitivity of separation and detection in capillary zone electrophoresis with laser-induced indirect fluorescence detection comprising the steps of:
  mixing an electrophoretic solution with a fluorescent buffer solution to present a mixture;

presenting a mixture to a capillary tube of a capillary zone electrophoresis system;

directing a laser beam to a portion of the capillary tube, the laser beam being stabilized before being directed to a portion of the capillary tube;

indirectly detecting the fluorescence from the mixture passing through portions of the capillary tube upon which the laser beam is imposed by measuring a signal independent of the spectral properties of the mixture but related to the change in fluorescence of the mixture relating to displacement or ion pairing of the electrophoretic solution and the fluorescent buffer solution; and detecting with high sensitivity, the constituent components of the electrophoretic solution by utilizing the indirect fluorescing measurements and without labeling the electrophoretic solution with a fluorescing portion.

9. A method of improving the sensitivity of separation and detection in capillary zone electrophoresis with laser-induced indirect fluorescence detection comprising the steps of:

mixing an electrophoretic solution with a fluorescent buffer solution to present a mixture;

presenting a mixture to a capillary tube of a capillary zone electrophoresis system;

directing a laser beam to a portion of the capillary tube, the laser beam being stabilized before being directed to a portion of the capillary tube;

indirectly detecting the fluorescence from the mixture passing through portions of the capillary tube upon which the laser beam is imposed by measuring a signal independent of the spectral properties of the mixture but related to the change in fluorescence of the mixture relating to displacement or ion pairing of the electrophoretic solution and the fluorescent buffer solution;

detecting with high sensitivity, the constituent components of the electrophoretic solution by utilizing the indirect fluorescing measurements and without labeling the electrophoretic solution with a fluorescing portion; and the laser-induced fluorescence from the mixture being filtered spatially before detection.

10. A method of improving the sensitivity of separation and detection in capillary zone electrophoresis with laser-induced indirect fluorescence detection comprising the steps of:

mixing an electrophoretic solution with a fluorescent buffer solution to present a mixture;

presenting a mixture to a capillary tube of a capillary zone electrophoresis system;

directing a laser beam to a portion of the capillary tube, the laser beam being stabilized before being directed to a portion of the capillary tube;

indirectly detecting the fluorescence from the mixture passing through portions of the capillary tube upon which the laser beam is imposed by measuring a signal independent of the spectral properties of the mixture but related to the change in fluorescence of the mixture relating to displacement or ion pairing of the electrophoretic solution and the fluorescent buffer solution;

detecting with high sensitivity, the constituent components of the electrophoretic solution by utilizing the indirect fluorescing measurements and without labeling the electrophoretic solution with a fluorescing portion; and the laser-induced fluorescence of the mixture being interface filtered before detection.

* * * * *

UNITED STATES PATENT AND TRADEMARK OFFICE
CERTIFICATE OF CORRECTION

PATENT NO. : 5,006,210
DATED : April 9, 1991
INVENTOR(S) : Edward S. Yeung, et al It is certified that error appears in the above-identified patent and that said Letters Patent is hereby corrected as shown below:

On the title page, in item [75]
The name(s) of the inventor(s) should read as follows:

EDWARD S. YEUNG and WERNER G. KUHR

There should be a space between Edward and the middle initial S.

at first page of specification after "[75] Inventors:".

at first page of specification under [19] it should read YEUNG, ET AL.

Signed and Sealed this

Eighteenth Day of August, 1992

Attest:

DOUGLAS B. COMER

Attesting Officer        Acting Commissioner of Patents and Trademarks